United States Patent [19]

Fukui

[11] Patent Number: 4,608,549
[45] Date of Patent: Aug. 26, 1986

[54] HYDROGEN-SELECTIVE SENSOR AND MANUFACTURING METHOD THEREFOR

[75] Inventor: Kiyoshi Fukui, Wakayama, Japan

[73] Assignee: New Cosmos Electric Co. Ltd., Japan

[21] Appl. No.: 564,446

[22] Filed: Dec. 22, 1983

[30] Foreign Application Priority Data

Dec. 28, 1982 [JP] Japan .................... 57-227568

[51] Int. Cl.$^4$ .......................... H01L 7/00; H01B 1/06
[52] U.S. Cl. ........................ 338/34; 252/578;
252/519; 252/520; 252/521; 427/82; 427/88;
427/91; 427/93; 427/94; 427/95
[58] Field of Search ............... 252/518, 519, 520, 521;
338/34, 35; 422/94–98; 73/27 R, 23; 427/82,
87, 88, 91, 93–95; 29/592 R

[56] References Cited

U.S. PATENT DOCUMENTS

| | | | |
|---|---|---|---|
| 3,903,226 | 9/1975 | Iga | 252/518 |
| 3,926,858 | 12/1975 | Ichinose | 252/521 |
| 4,045,764 | 8/1977 | Ichinose et al. | 338/34 |
| 4,347,495 | 8/1982 | Hunter et al. | 252/518 |

*Primary Examiner*—Josephine L. Barr
*Attorney, Agent, or Firm*—Jones, Tullar & Cooper

[57] ABSTRACT

A hydrogen-selective gas sensor comprising a gas-sensing element including a semiconductor in a principal portion thereof, and a thin coat or layer inactive for oxidation of hydrogen formed over an entire surface of the gas-sensing element or at least on a surface of the semiconductor. The thin layer comprises one of silicon oxide, aluminum oxide, and silicon nitride, and is formed on the surface of the semiconductor by chemical deposition, the thin layer checking passage of molecules other than hydrogen molecules.

6 Claims, 9 Drawing Figures

HYDROGEN-SELECTIVE SENSOR AND MANUFACTURING METHOD THEREFOR

BACKGROUND OF THE INVENTION

This invention relates to a hydrogen-selective sensor having a particularly high degree of sensitivity with respect to hydrogen gas and to a manufacturing method therefor.

It is well known that, for controlling burning conditions of burning equipment such as boilers, gas heaters and kerosene heaters, a highly selective sensor is used which readily detects one of the varied gaseous components of exhaust gas or incombustible gas discharged from this equipment, for example, oxygen, carbon monoxide, hydrogen, nitrogen oxides, sulphur oxides, carbon dioxide, water vapor, and hydrocarbon.

Of the above methods of detecting one of the gases with high sensitivity, the method of detecting hydrocarbon employs an FID (or hydrogen flame ionization detector) which has a high degree of detection sensitivity. In the method of detecting carbon monoxide or carbon dioxide, catalyzer nickel is used to reduce it to methane for high sensitivity detection.

In recent years hydrogen gas has been attracting attention as one of the clean energy sources and vigorous research has been conducted to develop effective methods of its generation, storage and utilization. There is a possibility of hydrogen gas being utilized for practical purposes as an important energy source in the future, but hydrogen gas is prone to explosion and so great care must be taken in its treatment.

Therefore hydrogen gas must be detected with high sensitivity, but the above methanization method utilizing FID has the disadvantage of being unable to detect hydrogen gas.

SUMMARY OF THE INVENTION

This invention has been made having regard to the foregoing situation. Therefore, an object of this invention is to form a thin coat or layer inactive for oxidation of hydrogen on a surface of a gas-sensing element, which coat permits easy passage of hydrogen molecules but checks passage of other molecules, thereby to reduce interference by the other molecules.

A further object of this invention is to provide a hydrogen-selective sensor comprising a thin coat or layer of a ceramic material inactive for oxidation of hydrogen formed on an entire surface of a gas-sensing element or at least on a surface of a semiconductor in the gas-sensing element, the ceramic material being one or more kinds of hydrogen permeable material selected preferably from the group consisting of silicone oxide ($SiO_2$), aluminum oxide ($Al_2O_3$) and silicon nitride ($Si_3N_4$), whereby hydrogen molecules are allowed to reach a central part or inner portion of the semiconductor.

According to this invention, the semiconductor in the gas-sensing element comprises a sintered piece preferably made from powder of metal oxides such as tin oxide ($SnO_2$). The thin ceramic coat is formed by applying, in vapor form, a silicon or aluminum compound which is to be thermally decomposed into a desired oxide or nitride, to the sintered piece under a desirable vapor pressure. At this time the silicon or aluminum compound becomes thermally decomposed and deposited on the surface of the sintered piece. This chemical vapor deposition process is carried out under strict control so that the resulting thin coat has a thickness and a fine structure permeable by hydrogen molecules.

According to this invention as described above, an excellent sensor having a sharp hydrogen-sensitivity is obtained by a relatively simple method and at low cost. According to a preferred embodiment of this invention in particular, the semiconductor in the gas sensing element retains its excellent porosity at the center portion although its surficial porosity is diminished by the thin ceramic coat. Therefore, a great advantage is obtained in that the hydrogen having passed the thin coat is detected by the gas-sensing element with a high degree of sensitivity. A further advantage is that this sensor is highly durable because the ceramic material forming the thin coat is chemically and thermally stable. There is no chance of the thin coat peeling off the sintered piece, owing to good compatibility between the ceramic material and the sintered piece or semiconductor. Thus, the sensor according to this invention provides highly reliable measurement data at all times.

Other objects and advantages of this invention will be apparent from the following description of the preferred embodiment to be made with reference to the drawings.

DETAILED DESCRIPTION OF THE PREFERRED EMBODIMENTS

Prior to describing an embodiment of this invention, an outline is described of a known example of gas-sensing element.

Figure 1:
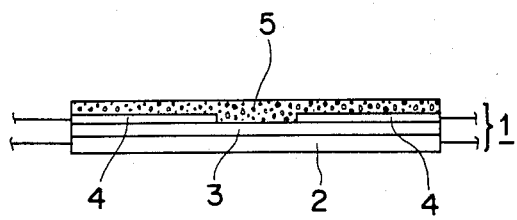
FIG. 1 is a partly broken away front view of a prior art construction.

FIG. 1 shows a configuration of one example of gas-sensing element used to manufacture a hydrogen-selective sensor according to this invention. This gas-sensing element 1 comprises a heater 2, a base plate 3 formed of alumina ($Al_2O_3$), both heater 2 and base plate 3 being dispensable, a pair of flat, forked vapor deposition layers 4 of platinum (Pt) printed on the base plate 3, and a piece of sintered metal oxide 5 such as tin oxide ($SnO_2$) coated on the base plate 3 and the vapor deposition layers 4. The vapor deposition layers 4 constitute electrodes of the element 1, and tin oxide forming the sintered piece 5 is a semiconductor.

A method of manufacturing the hydrogen-selective sensor 7 according to this invention is hereinafter described with reference to FIG. 2.

First, a silicon compound, trimethyl chlorosilane $((CH_3)_3SiCl)$, and the gas-sensing element 1 of FIG. 1 are made available for use.

Next, 1 ml of trimethyl chlorosilane is placed in a vessel which is put into a chamber having a 1 l (one liter) capacity. At the same time the gas-sensing element 1 heated to 550° C. is put into the chamber which is then sealed, and the chamber interior is maintained at room temperature for about 20 minutes. At this time the chamber is filled with a vapor of trimethyl chlorosilane of about 30 percent by volume under a fixed vapor pressure. Trimethyl chlorosilane immediately starts thermal decomposition on the surface of the sintered tin oxide of the heated gas-sensing element 1, as expressed by the following reaction formula:

$$(CH_3)_3SiCl + 6O_2 \rightarrow SiO_2 + HCl + 3CO_2 + 4H_2O$$

Figure 2:
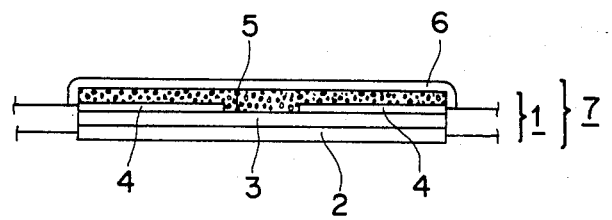
FIG. 2 is a partly broken away front view of a hydrogen-selective sensor according to one embodiment of this invention.
Figure 3:
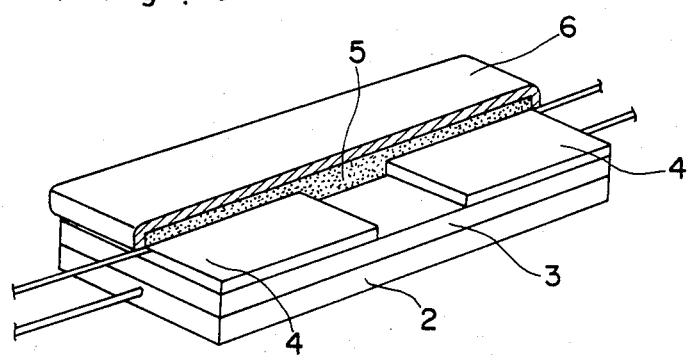
FIG. 3 is a partly broken away perspective view of the embodiment shown in FIG. 2.

By this reaction trimethyl chlorosilane undergoes chemical vapor deposition onto the surface of the sintered piece of tin oxide 5 and turns into a layer 6 of silicon oxide $(SiO_2)$ inactive for oxidation of hydrogen, realizing the hydrogen-selective sensor 7 as shown in FIGS. 2 and 3.

Figure 4:
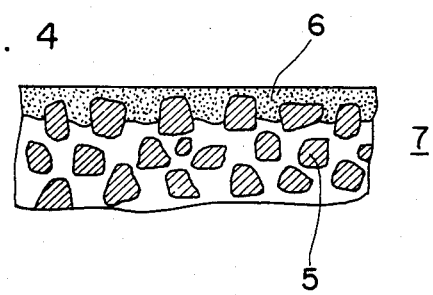
FIG. 4 is an enlarged illustrative view of a principal portion of FIG. 2.

The layer 6 of silicon oxide thus formed is a compact uniform layer overlying the surface of the sintered piece 5 of tin oxide, as shown in the enlarged view of FIG. 4.

In manufacturing the hydrogen-selective sensor 7 as described above, the silicon compound such as trimethyl chlorosilane is controlled at a predetermined temperature and a predetermined vapor pressure. Since the silicon compound is thermally decomposed on the surface of the porous sintered piece of tin oxide heated to a certain temperature and silicon oxide forms a thin layer thereon through chemical vapor deposition, the resulting sensor 7 is manufactured uniformly and easily. Therefore, according to the described method, fine cavities of varied sizes scattered over the surface of the sintered piece 5 of tin oxide are thoroughly filled by silicon oxide produced by the thermal decomposition, and the surface becomes coated with a very thin layer 6 of silicon oxide which is inactive for oxidation of hydrogen. The layer 6 thus formed is readily permeable by small size molecules such as hydrogen molecules but not by larger molecules. The hydrogen-selective sensor 7 thereby obtained has a high degree of sensitivity owing to the property of the silicon oxide layer 6 which permits easy passage of hydrogen molecules but checks passage of other molecules.

The silicon oxide layer 6 is very stable both chemically and thermally and is therefore highly durable.

In addition to silicon oxide as above, the layer or coat formed on the sintered piece 5 of tin oxide may comprise aluminum oxide $(Al_2O_3)$ or silicon nitride $(Si_3N_4)$. Alternatively, two or more layers of silicon oxide, aluminum oxide and silicon nitride may be placed one on top of another, or they may be subjected to vapor deposition simultaneously.

The highly sensitive hydrogen-selective sensor 7 is obtained by forming the described hydrogen selective layer 6 of silicon oxide or the like on the surface of the semiconductor which is not limited to the sintered piece of tin oxide 5 but may be any other material responsive to hydrogen.

Figure 5:
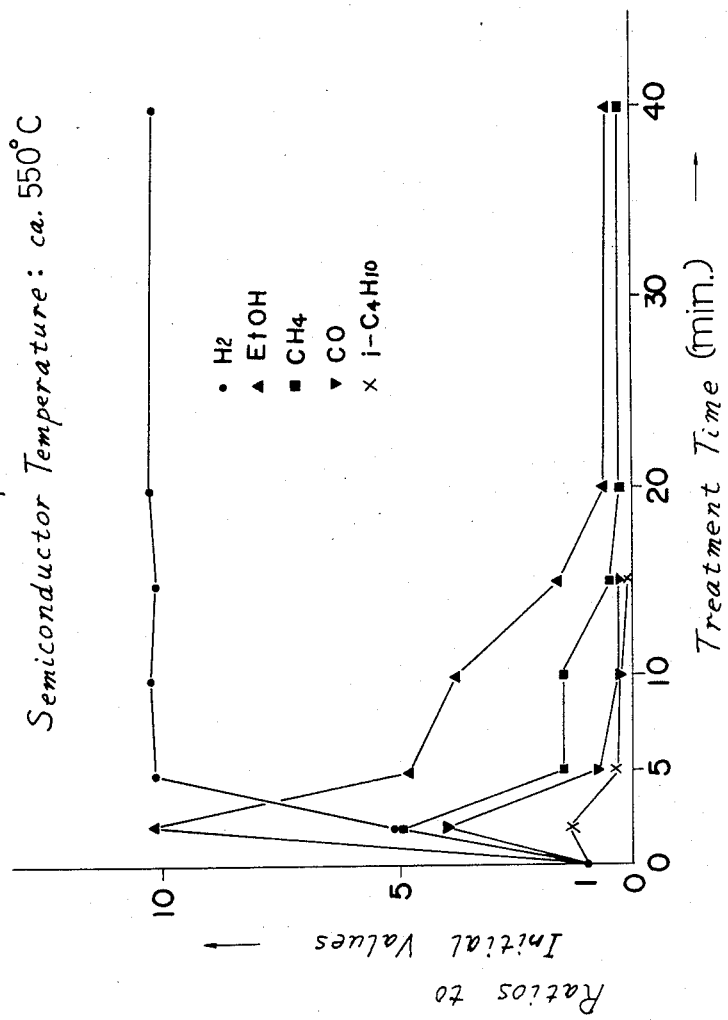
FIG. 5 is a graph showing a relationship between a treating time for a gas-sensing element and sensitivity of the hydrogen-selective sensor in respect of varied types of gas.

FIG. 5 is a graph showing a relationship between the treating time and sensitivity of the gas-sensing element with respect to varied types of gas. As seen in this graph, the sensitivity increases with respect to all types of gas during the initial period (for about two minutes). Thereafter, in about five minutes the sensitivity reaches the saturation point with respect to hydrogen, but lowers with respect to the other gases and levels off at certain values in about 20 minutes. It indicates that at this time a compact layer having a suitable thickness has been formed on the surface of the hydrogen-selective sensor 7 to permit easy passage of hydrogen only.

Figure 6B:
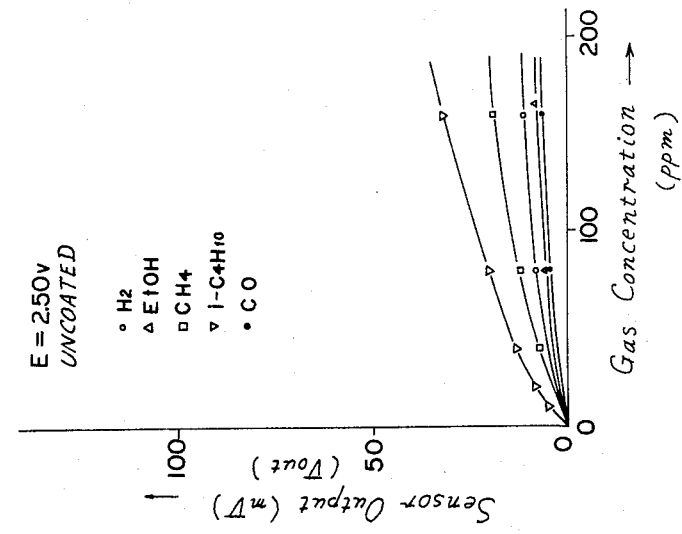
FIG. 6B is a graph showing the sensitivity of an untreated gas-sensing element without a thin coat.
Figure 6A:
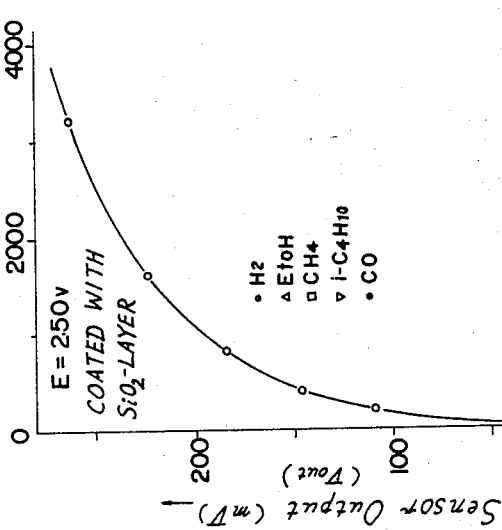
FIG. 6A is a graph showing the sensitivity of the hydrogen-selective sensor with respect to the varied types of gas.

A sensitivity curve of the hydrogen-selective sensor 7 thus manufactured with respect to the varied types of gas is shown in FIG. 6A. At the same time, a sensitivity curve of the gas-sensing element of the hydrogen-selective sensor 7 prior to the treatment is shown in FIG. 6B for comparison purposes.

Figure 7:
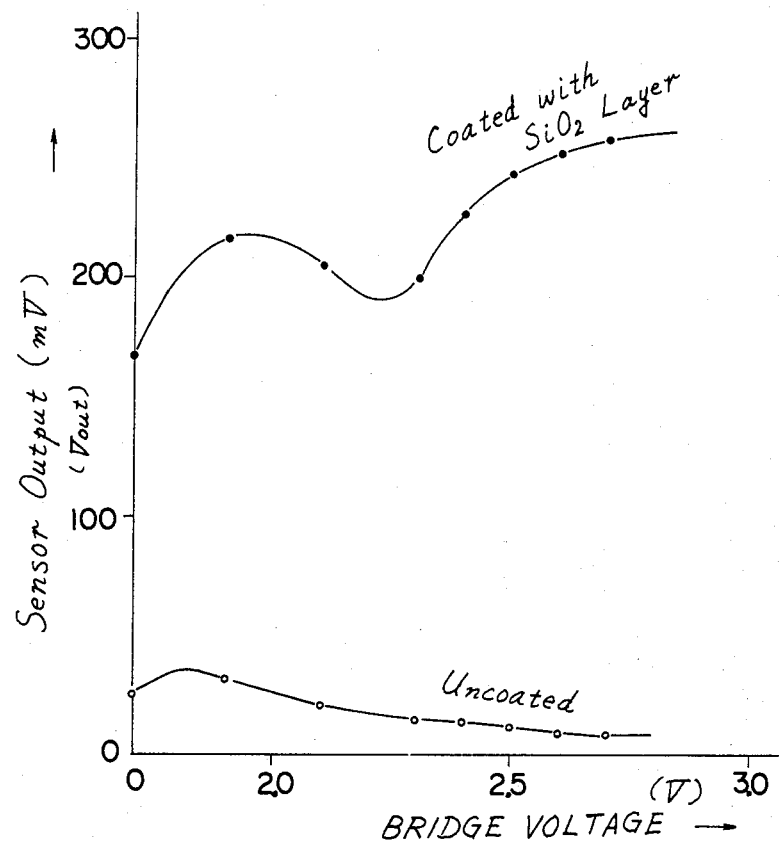
FIG. 7 is a graph showing dependency of the above sensor sensitivity on bridge voltage.

FIG. 7 is a graph showing dependency of the output voltage in the case of 100 ppm hydrogen gas on bridge voltage.

Figure 8:
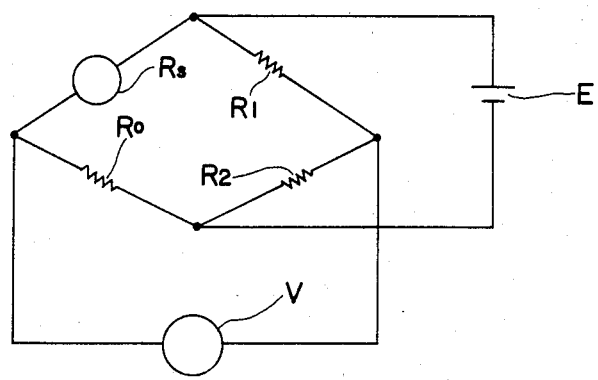
FIG. 8 is a view showing a measurement circuitry.

FIG. 8 is a view showing a measurement circuitry, in which reference Rs represents the semiconductor 5 of the hydrogen-selective sensor 7, $R_0$, $R_1$ and $R_2$ denote resistors having an equal value of resistance $R_0'$, E denotes an electric source, and V denotes a voltmeter.

As seen, the semiconductor Rs and the three resistors $R_0$, $R_1$ and $R_2$ form a bridge circuit, and a certain voltage E' is applied to one diagonal line thereof. At both ends of the other diagonal line, displacements from the electric potential equilibrium resulting from resistance value variations caused by the gas adsorption on the semiconductor Rs are taken out as the output voltage $\underline{V_{out}}$ of the sensor.

$$V_{out} = V_{gas} - V_{air}$$

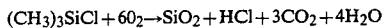

$$= -E'\left(\frac{Rs_1}{Rs_1 + R'_0} - \frac{Rs_0}{Rs_0 + R'_0}\right)$$

wherein $Rs_1$ is a resistance value of the semiconductor in the gas, $Rs_0$ is a resistance value of the semiconductor in the air, $\underline{V_{gas}}$ is an output voltage in the gas, and $\underline{V_{air}}$ is an output voltage in the air.

The semiconductor in the gas-sensing element 1 fit for use in this invention may comprise one of the following: $SnO_2$, $ZnO$, $Co_3O_4$, $WO_3$, $In_2O_3+Pt$, $\alpha\text{-}Fe_2O_3$, $BaTiO_3+Np_2O_3$.

Alkylhalogenoaluminum necessary for vaporization of the aluminum compounds include, for example, $(CH_3)_3Al_2Cl_3$, $(CH_3)_2AlCl$, $CH_3AlCl_2$, $(C_2H_5)_3Al_2Cl_3$, $(C_2H_5)_2AlCl$, and $C_2H_3AlCl_2$. Furthermore, aluminum alkoxides (i.e. alcoholates) include, for example, $Al(OC_2H_3)_3$ etc. Alkylaluminum compounds include, for example, $(CH_3)_3Al$, $(C_2H_5)_3Al$, $(i\text{-}C_3H_7)_3Al$, $(i\text{-}C_4H_9)_3Al$, and $(n\text{-}C_4H_9)_3Al$.

Material necessary for vaporization of the silicon compound may be selected from alkylsilicon compounds such as $(CH_3)_4Si$, $(CH_3)_2(C_2H_5)_2Si$, $(C_2H_5)_4Si$, $(C_6H_5)_3CH_3Si$, and $(CH_3)_2SiH_2$, alkylhalogenosilicon such as $(CH_3)_2SiCl_2$, $(CH_3)_2SiBr_2$, and $(CH_3)_3SiCl$, silicon alkoxides such as $Si(OCH_3)_4$ and $Si(OC_2H_5)_4$ or an oligomer thereof, $(CH_3)_3SiOH$, and $(CH_3)_3Si\text{-}OSi(CH_3)_3$, and silicon halides such as $SiCl_4$, $SiBr_4$ and $SiI_4$.

Furthermore, in order to form a layer of nitride, vapor of a silicon amide compound or the like may be decomposed in nitrogen gas.

What is claimed is:

1. A hydrogen-selective gas sensor comprising a gas-sensing element composed of a semiconductor, and a thin layer inactive for oxidation of hydrogen and formed on a surface of said gas-sensing element so as to cover same, the thin layer being selected from the group consisting of silicon oxide, aluminum oxide and silicon nitride, and the semiconductor comprising a sintered piece of metal oxide selected from the group consisting of $SnO_2$, $ZnO$, $Co_3O_4$, $WO_3$, $In_2O_3+Pt$, $\alpha$-$Fe_2O_3$ and $BaTiO_3+Np_2O_3$, wherein said thin layer has a diminished porosity to permit easy passage of hydrogen molecules, and to check passage of molecules of other gases greater than hydrogen molecules.

2. A gas sensor as defined in claim 1, wherein said thin layer is formed by causing a vapor to thermally decompose and deposit on said semiconductor heated to a predetermined temperature.

3. A method of manufacturing a hydrogen-selective sensor having a gas-sensing element including a semiconductor in a principal portion thereof, and a thin layer inactive for oxidation of hydrogen formed on a surface of said gas-sensing element, comprising a step of forming said thin layer of a ceramic material inactive for oxidation of hydrogen by causing a vapor thermally decomposable to produce a desired ceramic material to decompose on a surface of said gas-sensing element heated to a certain temperature, thereby depositing said ceramic material onto the surface of said gas-sensing element, said semiconductor of said gas-sensing element comprising a sintered piece of a metal oxide which is selected from the group consisting of $SnO_2$, $ZnO$, $Co_3O_4$, $WO_3$, $In_2O_3+Pt$, $\alpha$-$Fe_2O_3$ and $BaTiO_3+Np_2O_3$, wherein said ceramic material is selected from the group consisting of silicon oxide, aluminum oxide and silicon nitride.

4. A method as defined in claim 3, wherein said vapor comprises vapor of a compound selected from the group consisting of alkyl silicon halides, silicon alkoxides, silicon alkoxides oligomer, alkyl silicon, and silicon halides, which are thermally decomposable to produce a silicon oxide.

5. A method as defined in claim 3, wherein said vapor comprises vapor of a compound selected from the group consisting of alkyl aluminum halides, aluminum alkoxide, and alkylaluminum, which are thermally decomposable to produce an aluminum oxide.

6. A method as defined in claim 3, wherein said vapor comprises a silicon amide compound decomposable to produce a silicon nitride.

* * * * *